(12) United States Patent
Hulteen et al.

(10) Patent No.: US 8,817,265 B2
(45) Date of Patent: Aug. 26, 2014

(54) OPTOELECTRONIC METHODS AND DEVICES FOR DETECTION OF ANALYTES

(71) Applicant: 3M Innovative Properties Company, St. Paul, MN (US)

(72) Inventors: John C. Hulteen, Afton, MN (US); Kiran S. Kanukurthy, Cottage Grove, MN (US); Neal A. Rakow, Woodbury, MN (US); Andrzej F. Rybacha, Coquitlam (CA); Richard L. Rylander, Stillwater, MN (US); Arthur Scheffler, Surrey (CA); Zeljko Zupanc, Richmond (CA)

(73) Assignee: 3M Innovative Properties Company, St. Paul, MN (US)

( * ) Notice: Subject to any disclaimer, the term of this patent is extended or adjusted under 35 U.S.C. 154(b) by 2 days.

(21) Appl. No.: 14/043,553

(22) Filed: Oct. 1, 2013

(65) Prior Publication Data

US 2014/0036270 A1 Feb. 6, 2014

Related U.S. Application Data

(62) Division of application No. 12/728,883, filed on Mar. 22, 2010, now Pat. No. 8,576,400.

(60) Provisional application No. 61/164,496, filed on Mar. 30, 2009.

(51) Int. Cl.
*G01N 21/55* (2014.01)
*G01N 21/78* (2006.01)
*G01N 21/27* (2006.01)

(52) U.S. Cl.
CPC .............. *G01N 21/55* (2013.01); *G01N 21/783* (2013.01); *G01N 21/274* (2013.01)
USPC ..................... 356/445; 250/459.1; 250/458.1; 356/320; 356/337

(58) Field of Classification Search
CPC .... G01N 21/274; G01N 21/55; G01N 21/783
USPC ............ 250/459.1, 458.1; 356/320, 445, 417, 356/337; 436/172, 164; 422/82.05, 82.08
See application file for complete search history.

(56) References Cited

U.S. PATENT DOCUMENTS

| 4,205,043 A | 5/1980 | Esch et al. |
| 4,680,165 A | 7/1987 | Vo-Dinh |

(Continued)

FOREIGN PATENT DOCUMENTS

| CN | 1507560 A | 6/2004 |
| JP | 2008-039787 | 2/2008 |

(Continued)

OTHER PUBLICATIONS

International Search Report, PCT/US2010/028074, Mar. 20, 2010, 4 pages.

*Primary Examiner* — Tarifur Chowdhury
*Assistant Examiner* — Iyabo S Alli
(74) *Attorney, Agent, or Firm* — Kenneth B. Wood

(57) ABSTRACT

Herein are disclosed optoelectronic methods and devices for detecting the presence of an analyte. Such methods and devices may comprise at least one sensing element that is responsive to the presence of an analyte of interest and that may be interrogated optically by the use of at least one light source and at least one light detector.

19 Claims, 7 Drawing Sheets

(56) References Cited

U.S. PATENT DOCUMENTS

| | | |
|---|---|---|
| 4,913,881 A | 4/1990 | Evers |
| 5,091,642 A | 2/1992 | Chow et al. |
| 5,364,593 A | 11/1994 | Mihaylov et al. |
| 5,396,325 A | 3/1995 | Carome et al. |
| 5,563,707 A | 10/1996 | Prass et al. |
| 5,728,352 A | 3/1998 | Poto |
| 5,822,473 A | 10/1998 | Magel et al. |
| 5,843,692 A | 12/1998 | Phillips |
| 6,172,759 B1 | 1/2001 | Goldstein |
| 6,284,198 B1 | 9/2001 | Kirollos et al. |
| 6,822,215 B2 | 11/2004 | Hensel |
| 6,838,289 B2 * | 1/2005 | Bell et al. .................. 250/459.1 |
| 6,985,818 B1 | 1/2006 | Samuels |
| 7,135,342 B2 * | 11/2006 | Colvin et al. ................ 436/164 |
| 7,201,878 B2 | 4/2007 | Lin |
| 2004/0062682 A1 | 4/2004 | Rakow et al. |
| 2004/0184948 A1 | 9/2004 | Rakow et al. |
| 2004/0189982 A1 | 9/2004 | Galarneau et al. |
| 2007/0140907 A1 | 6/2007 | Rakow et al. |
| 2007/0190655 A1 | 8/2007 | Yanagisawa |
| 2007/0238192 A1 | 10/2007 | Locke |
| 2007/0274860 A1 | 11/2007 | Nakano |
| 2007/0297944 A1 | 12/2007 | Wendland et al. |
| 2008/0063575 A1 | 3/2008 | Rakow et al. |
| 2008/0063874 A1 | 3/2008 | Rakow et al. |
| 2008/0095664 A1 | 4/2008 | Chopra et al. |

FOREIGN PATENT DOCUMENTS

| | | |
|---|---|---|
| JP | 2008-249609 | 10/2008 |
| RU | 1672817 | 5/1993 |
| RU | 2262685 | 10/2005 |
| WO | WO 91/11136 | 8/1991 |
| WO | WO 2004/063393 A1 | 7/2004 |
| WO | WO 2007/075443 | 7/2007 |

* cited by examiner

OPTOELECTRONIC METHODS AND DEVICES FOR DETECTION OF ANALYTES

BACKGROUND

The ability to detect chemical analytes, especially organic chemical analytes, is important in many applications, including environmental monitoring and the like. Such detection and/or monitoring of analytes may find particular use in, for example, personal monitors (e.g., that can be worn or carried by a person), and/or area monitors (e.g., that can be placed in a desired environment).

Many methods for the detection of chemical analytes have been developed, for example optical, gravimetric, microelectromechanical, and colorimetric. Though colorimetric devices currently exist for a range of analytes, most are based upon employing dyes or colored chemical indicators for detection. Such compounds are typically selective, meaning that multiple sensors may be necessary in order to detect various classes of compounds. Moreover, many of these systems have lifetime limitation issues, due to photo-bleaching or undesirable side reactions. Many such systems also rely on complicated or bulky optoelectronic components to carry out the optical interrogation.

SUMMARY OF THE INVENTION

Herein are disclosed optoelectronic methods and devices for detecting the presence of an analyte. Such methods and devices may comprise at least one sensing element that is responsive to the presence of an analyte of interest and that may be interrogated optically as described herein.

In one aspect, disclosed herein is a method of monitoring an analyte in an atmosphere, comprising: exposing at least one sensing element to an atmosphere potentially containing an analyte for a period of time; directing light in a first wavelength range onto the at least one sensing element and obtaining a first signal that is representative of an amount of light in the first wavelength range reflected from the at least one sensing element; directing light in a second wavelength range onto the at least one sensing element and obtaining a second signal that is representative of the amount of light in the second wavelength range reflected from the at least one sensing element; comparing the first and second signals to provide a compared signal; and, correlating the compared signal to a predetermined response curve and thereby obtaining a concentration value that is associated with the concentration of the analyte in the monitored atmosphere.

In another aspect, herein is disclosed an optoelectronic device for monitoring an analyte in an atmosphere, comprising: a housing at least partially defining an interior space and containing at an opening; at least one disposable sensing element located in the interior space or in the opening of the housing; in the interior space, at least one light source arranged to direct light onto the sensing element and at least one light detector arranged to measure an amount of light reflected by the sensing element, wherein the at least one light source and the at least one light detector are arranged in a side by side coplanar configuration on a common printed circuit board contained within the interior space of the device.

In another aspect, herein is disclosed an optoelectronic device for monitoring an analyte in an atmosphere, comprising: a housing at least partially defining an interior space and containing at an opening; at least one sensing element secured in the opening of the housing; and, in the interior space, at least one light source arranged to direct light onto the sensing element and at least one light detector arranged to measure an amount of light reflected by the sensing element, wherein when the sensing element is secured in the opening of the housing the opening is occluded such that the interior space of the device comprises a sealed interior space.

These and other aspects of the invention will be apparent from the detailed description below. In no event, however, should the above summaries be construed as limitations on the claimed subject matter, which subject matter is defined solely by the attached claims, as may be amended during prosecution.

Like reference symbols in the various figures indicate like elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "outward", "inward", "up" and "down", and "first" and "second" may be used in this disclosure, it should be understood that those terms are used in their relative sense only unless otherwise noted.

DETAILED DESCRIPTION

Figure 1:
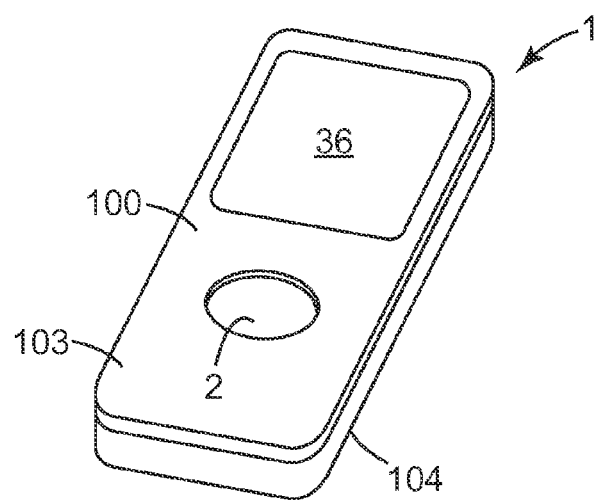
FIG. 1 is a perspective view of an exemplary optoelectronic device.

Shown in perspective view in FIG. 1 is an exemplary optoelectronic device 1 comprising at least one optically interrogatable sensing element 2. Device 1 may be used for the monitoring of a gaseous environment, typically an air atmosphere.

In some embodiments device 1 may be worn on or adjacent to a portion of the body and/or clothing of a person, for example if device 1 is to function as a personal monitor. In such cases, device 1 may be attached (e.g., by a clip, loop, strap, sleeve, lanyard, pocket protector, etc., not shown in FIG. 1) to the persons' clothing or otherwise worn or carried, e.g. as a badge. Device 1 may also be used for area monitoring, for example by being placed into an environment (e.g., a room, vehicle, etc.), which may be indoors or outdoors, in which it is desired to monitor the presence of an analyte. Device 1 may comprise housing 100 which may comprise any suitable shape, size or form. Housing 100 may for example comprise at least first major surface 103 that faces generally away from a wearer's body or a wall and second major surface 104 that faces generally toward the wearer's body or a wall.

In some embodiments, methods and/or devices disclosed herein may be used in connection with a respiratory protection device (e.g., a respirator, such as might contain a filter element, sorbent media, etc., for removal of certain substances from an atmosphere), to provide a so-called end of service life indicator (ESLI) that can monitor the remaining sorptive capacity of a filter element, bed of sorbent media, etc.

Sensing element 2 is responsive to the presence of an analyte and may be interrogated optically as discussed later herein. Sensing element 2 exhibits a reflectance spectrum that comprises one or more peaks and valleys at different wavelengths and that may change in the presence of an analyte or upon a change in the concentration of an analyte. In one embodiment, the light reflected from sensing element 2 is specularly reflected. In another embodiment, the light reflected from sensing element 2 is diffusely reflected. Sensing element 2 contains at least one analyte-responsive layer whose optical properties (e.g., optical thickness) are responsive to the presence of an analyte. Sensing element 2 may further contain at least one layer that is reflective and/or at least one layer that is semireflective (as described in detail later herein). In some embodiments, sensing element 2 may comprise an analyte-responsive layer 230 in between a reflective layer 240 and a semireflective layer 220, the layers combining to comprise a so-called interference filter exhibiting a reflectance spectrum that may change in the presence of an analyte or upon a change in the concentration of an analyte.

Figure 2:
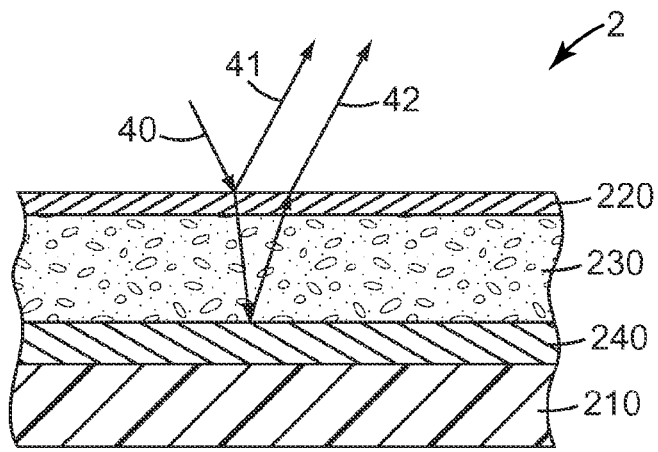
FIG. 2 is a side cross sectional view of a portion of an exemplary sensing element.

An exemplary sensing element 2 is shown in FIG. 2. In embodiments incorporating this design, sensing element 2 comprises in order semireflective layer 220, analyte-responsive layer 230, reflective layer 240, and substrate 210. In interrogation of sensing element 2, light rays 40 (e.g., from light source 31, described later herein) impinge on semireflective layer 220. Some portion of light rays 40 may reflect from semireflective layer 220 as light rays 41. Some portion of light rays 40 may pass through semireflective layer 220 and pass through analyte-responsive layer 230 and reflect from reflective layer 240, to emerge from sensing element 2 as light rays 42. Light rays 41 and 42 may combine to collectively form a reflectance spectrum that may change in the presence of an analyte or upon a change in the concentration of an analyte.

In the exemplary design of FIG. 2, analyte may permeate through semireflective layer 220 to enter analyte-responsive layer 230. This may change the optical properties of layer 230 (e.g., the optical thickness) such that the reflectance spectrum of light reflected from sensing element 2 may change sufficiently to allow the presence of, and/or the concentration of, an analyte to be detected or monitored.

In a embodiments incorporating the design shown in FIG. 2, semireflective layer 220 is analyte-permeable, which property can be provided as discussed later herein, and is in fluid communication with analyte-responsive layer 230, such that analyte can enter layer 230 through layer 220. In the design of FIG. 2, reflective layer 240 may or may not be analyte-permeable. In the design of FIG. 2, light may not need to pass through, or interact with, substrate 210, during optical interrogation of sensing element 2, so substrate 210 may not need any particular optical property (e.g., transparency).

Figure 3:
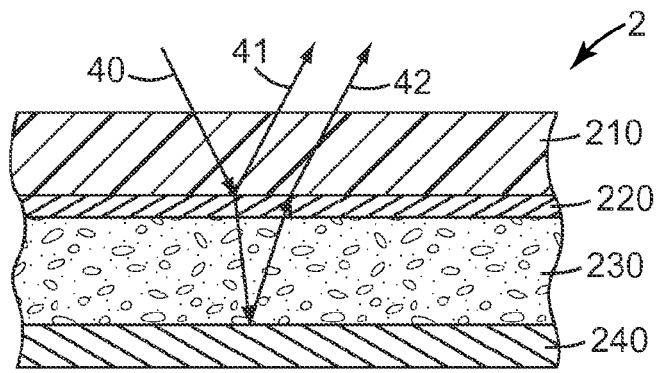
FIG. 3 is a side cross sectional view of a portion of an exemplary sensing element.

Another exemplary sensing element 2 is shown in FIG. 3. In embodiments incorporating the design shown in FIG. 3, sensing element 2 comprises in order (optional) substrate 210, semireflective layer 220, analyte-responsive layer 230, and reflective layer 240. Light rays 40 impinge on and pass through substrate 210. Some portion of light rays 40 may reflect from semireflective layer 220 to emerge from sensing element 2 as light rays 41. Some portion of light rays 40 may pass through semireflective layer 220 and pass through analyte-responsive layer 230 and reflect from reflective layer 240, to emerge from sensing element 2 as light rays 42. Light rays 41 and 42 may combine to collectively form a reflectance spectrum that may change in the presence of an analyte or upon a change in the concentration of an analyte.

In the exemplary design of FIG. 3, analyte may permeate through reflective layer 240 to enter analyte-responsive layer 230. This may change the optical properties of layer 230 (e.g., the optical thickness) such that the reflectance spectrum of light reflected from sensing element 2 may change sufficiently to allow the presence of, and/or the concentration of, an analyte to be detected or monitored. In embodiments incorporating the design shown in FIG. 3, reflective layer 240 is analyte-permeable, which property can be provided through methods discussed later herein, and is in fluid communication with analyte-responsive layer 230. In the design of FIG. 3, semireflective layer 220 may or may not be analyte-permeable. In the exemplary design of FIG. 3, light may pass through substrate 210, so substrate 210 should be optically clear at the wavelengths of interest.

In embodiments incorporating the design shown in FIG. 2, semireflective layer 220 may be permeable to the analyte, thus the analyte may enter sensing element 2 on the same side as which sensing element 2 is optically interrogated. In such a case, sensing element 2 may be conveniently positioned (as shown in the exemplary design of FIG. 4) within interior space 125 of housing 100 of device 1 (e.g., held by one or more support brackets 177), with sensing element 2 being optically connected to at least one light source 31 and at least one light detector 32. By optically connected is meant that sensing element 2 is capable of receiving light from light source 31, and light detector 32 is capable of receiving light reflected from sensing element 2, either directly (e.g., in the event that the components face each other directly, as in the exemplary embodiment of FIG. 4), or by means of one or more mirrors. In such embodiments one or more non-occluded openings 101 may be provided in housing 100 so that analyte can enter interior space 125 of housing 100 so as to be able to reach analyte-permeable layer 220 of sensing element 2. While in FIG. 4 sensing element 2 is shown as positioned adjacent to non-occluded opening 101 in front major surface 103 of housing 100, facing light source 31 and light detector 32 which are positioned side by side adjacent second major surface 104 of housing 100, many other configurations are possible. For example, light source 31 and light detector 32 may be spaced apart; mirrors may be used to optically connect sensing element 2 with light source 31 and/or light detector 32; sensing element 2 may not be positioned adjacent opening 101, and so on.

In embodiments incorporating the design shown in FIG. 3, reflective layer 240 may be permeable to the analyte, thus the analyte may enter sensing element 2 from the opposite side from which sensing element 2 is optically interrogated. In such embodiments, sensing element 2 may be conveniently positioned (as shown in the exemplary design of FIG. 5) in, or adjacent to, occluded opening 102 in housing 100 of device 1, with analyte-permeable reflective layer 240 of sensing element 2 facing outward (i.e., away from interior space 125), and with the optically interrogatable side of sensing element 2 facing into interior space 125 such that sensing element 2 is optically connected to at least one light source 31 and at least one light detector 32. In such embodiments, sensing element 2 and/or other layers provided along with sensing element 2 can act to occlude (seal) opening 102 such that interior space 125 comprises sealed interior space 126. In such embodiments, sensing element 2 may comprise at least one optically clear, analyte-impermeable substrate 210 (described later herein in detail) that is located between analyte-responsive layer 230 of sensing element 2 and sealed interior space 126.

Properties, methods of making, and so on, of analyte-responsive layer 230, and, if present, of substrate 210, semi-reflective layer 220, and/or reflective layer 240 will now be discussed in further detail. Such properties are understood to be applicable to the making of reflective sensing elements in general and in particular to either of the exemplary embodiments disclosed above with reference to FIGS. 2 and 3, except where specified to be applicable to a particular embodiment. Even though the same reference numbers are used to designate the above-referenced layers, those of ordinary skill in the art will readily appreciate that the layers so designated may have the same or different configurations and/or compositions. Various other layers, including for example tie layers, adhesion promoting layers, protective layers, cover layers, and the like, may be included in sensing element 2 as desired, as long as they do not unacceptably interfere with the functioning of sensing element 2. In addition, all designs, configurations and features of device 1 discussed herein, are understood to be applicable to either of the above embodiments unless stated otherwise.

Analyte-responsive layer 230 can be comprised of any material that is sufficiently permeable to an analyte of interest, and whose optical thickness changes sufficiently upon exposure to the analyte, to allow the desired functioning of sensing element 2 as described herein. In some embodiments, analyte-responsive layer comprises a porous material. In this context, "porous" means that the material comprises internal pores that are at least partially interconnected. Materials may be chosen, for example, with an average (mean) pore size (as characterized, for example, by sorption isotherm procedures) of less than about 100 nm. In various embodiments, materials may be chosen with an average pore size of less than 20 nm, less than about 10 nm, or less than about 2 nm. Layer 230 may be homogeneous or heterogeneous, and may, for example, be made from one or more inorganic components, one or more organic components, or a mixture of inorganic and organic components. Representative inorganic materials that may be used in layer 230 include metal oxides, metal nitrides, metal oxynitrides and other inorganic materials that can be formed into transparent (and if desired porous) layers of appropriate thickness for producing a suitable optical response. For example, layer 230 may comprise silicon oxides, silicon nitrides, silicon oxynitrides, aluminum oxides, titanium oxides, titanium nitride, titanium oxynitride, tin oxides, zirconium oxides, zeolites or combinations thereof.

Porous silica may be an especially desirable inorganic analyte-responsive layer material. Porous silicas may be prepared, for example, using a sol-gel processing route and made with or without an organic template. Exemplary organic templates include surfactants, e.g., anionic or nonionic surfactants such as alkyltrimethylammonium salts, poly(ethyleneoxide-co-propylene oxide) block copolymers and other surfactants or polymers. The sol-gel mixture may be converted to a silicate and the organic template may be removed to leave a network of pores within the silica. A variety of organic molecules may also be employed as organic templates. For example, sugars such as glucose and mannose may be used as organic templates to generate porous silicates. Organo-substituted siloxanes or organo-bis-siloxanes may be included in the sol-gel composition to render the micropores more hydrophobic and limit sorption of water vapor. Plasma chemical vapor deposition may also be employed to generate porous inorganic analyte-responsive materials. This methodology generally involves forming a plasma from gaseous precursors, depositing the plasma on a substrate to form an amorphous random covalent network layer, and then heating the amorphous covalent network layer to form a porous amorphous random covalent network layer. Such methods and materials are described in further detail in International (PCT) Patent Application US 2008/078281, titled ORGANIC CHEMICAL SENSOR COMPRISING PLASMA-DEPOSITED MICROPOROUS LAYER, AND METHOD OF MAKING AND USING, which is incorporated by reference herein for this purpose.

In some embodiments, analyte-responsive layer 230 is comprised at least in part of organo-silicate materials, herein defined as compositions that are hybrids containing a covalently linked three dimensional silica network (—Si—O—Si—) with some organo-functional groups R, where R is a hydrocarbon or heteroatom substituted hydrocarbon group linked to the silica network by at least one Si—C bond. Such materials and methods of their making are described in further detail in U.S. Provisional Application Ser. No. 61/140,180, titled ORGANIC CHEMICAL SENSOR WITH MICROPOROUS ORGANOSILICATE MATERIAL, which is incorporated by reference herein for this purpose.

Representative organic materials that may be used to form layer 230 include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof.

In some embodiments, analyte-responsive layer 230 is made at least partially from components chosen from the family of materials comprising so-called "polymers of intrinsic microporosity" (hereafter called PIMs). Polymers in this family are described and characterized in, for example, "Polymers of Intrinsic Microporosity (PIMs): Robust, Solution-Processable, Organic Microporous Materials," Budd et al., *Chem. Commun.*, 2004, pp. 230-231; in "Polymers of Intrinsic Microporosity (PIMs)," McKeown et al., *Chem. Eur. J.*, 2005, 11, No. 9, 2610-2620; in US Patent Application Publication 2006/0246273 to McKeown et al.; and in Published PCT application No. WO 2005/012397A2 to McKeown et al., all of which are incorporated by reference herein for this purpose.

PIMs can be formulated via the use of any combination of monomers that lead to a very rigid polymer within which there are sufficient structural features to induce a contorted structure. In various embodiments, PIMs can comprise organic macromolecules comprised of generally planar species connected by rigid linkers, said rigid linkers having a point of contortion such that two adjacent planar species connected by the linker are held in non-coplanar orientation. In further embodiments, such materials can comprise organic macromolecules comprised of first generally planar species connected by rigid linkers predominantly to a maximum of two other said first species, said rigid linkers having a point of contortion such that two adjacent first planar species connected by the linker are held in non-coplanar orientation. In various embodiments, such a point of contortion may comprise a spiro group, a bridged ring moiety or a sterically congested single covalent bond around which there is restricted rotation.

In a polymer with such a rigid and contorted structure, the polymer chains are unable to pack together efficiently, thus the polymer possesses intrinsic microporosity. Thus, PIMs have the advantage of possessing microporosity that is not significantly dependent on the thermal history of the material. PIMs thus may offer advantages in terms of being reproducibly manufacturable in large quantities, and in terms of not exhibiting properties that change upon aging, shelf life, etc.

For many applications, analyte-responsive layer 230 may be hydrophobic. This may reduce the chance that water vapor (or liquid water) will cause a change in the response of layer 230 and interfere with the detection of an analyte, for example, the detection of organic solvent vapors.

Further details and attributes of suitable materials useful for analyte responsive layer 230, and methods of making layer 230 from such materials, are described in e.g., U.S. Published Patent Application No. 2008/0063874, which is incorporated by reference herein for this purpose.

Sensing element 2 may comprise reflective layer 240. In some embodiments, reflective layer 240 may be deposited (e.g., by various methods described herein) upon the surface of a previously formed analyte-responsive layer 230; or, reflective layer 240 may be deposited onto substrate 210, with analyte-responsive layer 230 then being deposited onto reflective layer 240.

Reflective layer 240 may comprise any suitable material that can provide sufficient reflectivity. Suitable materials for the reflective layer may include metals or semi-metals such as aluminum, chromium, gold, nickel, silicon, and silver. Other suitable materials that may be included in the reflective layer may include metal oxides. In some embodiments, the reflective layer may be at least about 90% reflective (i.e., at most about 10% transmissive), and in some embodiments, about 99% reflective (i.e., about 1% transmissive), at a wavelength of about 500 nm.

In some embodiments (e.g., incorporating the design of FIG. 3), reflective layer 240 may advantageously be permeable to an analyte of interest. This may be provided, for example, by forming reflective layer 240 of metal nanoparticles arranged in a morphology which approximates a stack of cannonballs or marbles and through which the analyte can permeate to reach and enter analyte-responsive layer 230.

A variety of metal nanoparticles may be employed. Representative metals include silver, nickel, gold, platinum and palladium and alloys containing any of the foregoing. Metals prone to oxidation when in nanoparticle form (e.g., aluminum) might be used but desirably would be avoided in favor of less air-sensitive metals. The metal nanoparticles may be monolithic throughout or may have a layered structure (e.g., a core-shell structure such as an Ag/Pd structure). The nanoparticles may, for example, have an average particle diameter of about 1 to about 100, about 3 to about 50 or about 5 to about 30 nm. The overall thickness of the metal nanoparticle layer may, for example, be less than about 200 nm or less than about 100 nm, and the minimum layer thickness may, for example, be at least about 5 nm, at least about 10 nm or at least about 20 nm. Although large diameter microparticles might be applied to form a monolayer, the nanoparticle layer typically will be several nanoparticles thick, e.g., at least 2 or more, 3 or more, 4 or more or 5 or more nanoparticles, and with up to 5, up to 10, up to 20 or up to 50 nanoparticles total thickness. The metal nanoparticle reflective layer may, for example, have a reflectance of at least about 40%, at least about 50% or at least about 60% at 500 nm. In various embodiments, the metal nanoparticle reflective layer may have a reflectance of at least about 80%, of at least about 90%, or of about 99%, at a wavelength of about 500 nm.

Solutions or suspensions of suitable metal nanoparticles are available from several suppliers, including Inkjet Silver Conductor ink AG-IJ-G-100-S1 (from Cabot Printable Electronics and Displays); SILVERJET™ DGH 50 and DGP 50 ink (from Advanced Nano Products); SVW001, SVW102, SVE001, SVE102, NP1001, NP1020, NP1021, NP1050 and NP1051 inks from Nippon Paint (America); METALON™ FS-066 and JS-011 inks from Novacentrix Corp. and NP Series nanoparticle paste from Harima Chemicals, Inc. The metal nanoparticles may be borne in a variety of carriers, including water and organic solvents. The metal nanoparticles may also be borne in a polymerizable monomeric binder but desirably such binder is removed from the applied coating (using e.g., solvent extraction or sintering) so as to provide a permeable nanoparticle layer.

Layer 240 may be formed by applying a dilute coating solution or suspension of metal nanoparticles to analyte-responsive layer 230 and allowing the solution or suspension to dry to form permeable reflective layer 240. The dilution level may, for example, be such as to provide a coating solution or suspension that will provide a suitably liquid- or vapor-permeable metal nanoparticle layer, for example solids levels less than 30 wt. %, less than 20 wt. %, less than 10 wt. %, less than 5% or less than 4%. By diluting an as-received commercial metal nanoparticle product with additional solvent and applying and drying the dilute solution or suspension, an appreciably thin, liquid- or vapor-permeable layer can be obtained. A variety of coating techniques can be employed to apply the metal nanoparticle solution or suspension, including swabbing, dip coating, roll coating, spin-coating, spray coating, die coating, ink jet coating, screen printing (e.g., rotary screen printing), gravure printing, flexographic printing and other techniques that will be familiar to persons having ordinary skill in the art. Spin-coating may provide a thinner, more permeable coating than is obtained using other methods. Accordingly, some silver nanoparticle suspensions available at low solids levels (such as 5 wt. % SVW001 silver from Nippon Paint or 10 wt. % SILVERJET DGH-50 or DGP-50 from Advanced Nano Products) might be usable in the as-received form without further dilution if spin-coated at an appropriately high speed and temperature onto a suitable substrate. The metal nanoparticle layer may be sintered after it has been applied (e.g., by heating at about 125 to about 250 degrees C. for about 10 minutes to about 1 hour) so long as the sintering does not cause a loss of adequate permeability. It will be understood that the resulting reflective layer may no longer contain readily-identifiable nanoparticles, but that it may be referred to as a nanoparticle reflective layer to identify the manner in which it has been made.

Further details and attributes of suitable analyte-permeable materials useful for reflective layer 240, in particular metal nanoparticle materials, are described in e.g., U.S. Published Patent Application No. 2008/0063874, which is incorporated by reference herein for this purpose.

Sensing element 2 may comprise semireflective layer 220. In various embodiments, semireflective layer 220 may be deposited (e.g., by various methods described herein) upon the surface of a previously formed analyte-responsive layer 230; or, semireflective layer 220 may be deposited onto substrate 210, with analyte-responsive layer 230 then being deposited onto semireflective layer 220.

Semireflective layer 220 by definition will comprise a lower reflectivity than does reflective layer 240. Semireflective layer 220 can comprise any suitable material that can provide appropriate semireflectivity (e.g., when at an appropriate thickness). Suitable materials may include metals or semi-metals such as aluminum, chromium, gold, nickel, silicon, and silver. Other suitable materials may include metal oxides.

In various embodiments, semireflective layer 220 may be about 30 to about 70% reflective, or from about 40 to about 60% reflective, at a wavelength of about 500 nm.

In some embodiments (e.g., of the type incorporating the design of FIG. 2), semireflective layer 220 may advantageously be permeable to an analyte of interest. Thus, in this case it may be preferable to provide semireflective layer 220 at an appropriate thickness in order to provide appropriate reflectivity while permitting an analyte to permeate through semireflective layer 220 to reach and enter analyte-responsive layer 230. In some cases, a thickness in the general range of 5 nm may be desired (e.g., if semireflective layer 220 is deposited by vapor deposition to form a metal layer). Specific desired thicknesses will depend on the material used to form the layer, the analyte to be detected, and may be configured as necessary.

Semireflective layer 220 and reflective layer 240 may be made from similar or the same materials (e.g., deposited at different thicknesses or coating weights, so as to impart the desired differences in reflectivity). Semireflective layer 220 and reflective layer 240 may be continuous or discontinuous, as long as the properties of reflectivity and permeability that are desired for a particular application are provided. Further details of suitable semireflective layers and reflective layers, their properties and methods of making, are described for example in U.S. Published Patent Application 2008/0063874, incorporated by reference herein for this purpose.

Substrate 210, if present, may be comprised of any suitable material (e.g., glass, plastic, etc.) capable of providing support for the sensing element. In embodiments in which light passes through substrate 210 in order for sensing element 2 to be interrogated, substrate 210 should be optically clear (i.e., should comprise sufficient transparency at the wavelengths of interest) and should not have other properties (e.g., fluorescence) that would unacceptably affect the optical signal. In some embodiments substrate 210 comprises a barrier material that is impermeable to analyte and/or to other substances (e.g., gas, vapor, or solid). Certain polymeric substrates (e.g., semicrystalline polymers, etc.) may possess particularly enhanced barrier properties. Other polymeric substrates (e.g., glassy polymers such as polycarbonate, polystyrene, and the like), while not having barrier properties the equal of e.g. polyester, may still be sufficiently impermeable that they may be used in the present application.

Figure 4:
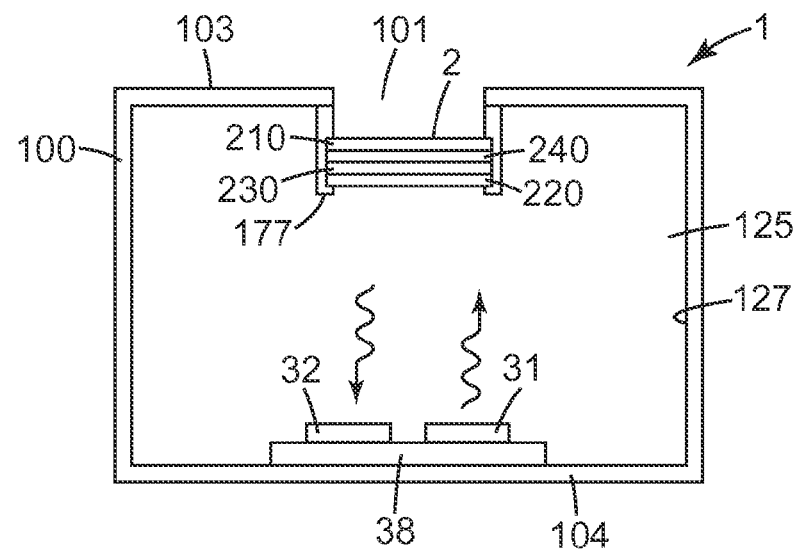
FIG. 4 is a side schematic cross sectional view of an exemplary optoelectronic device.
Figure 5:
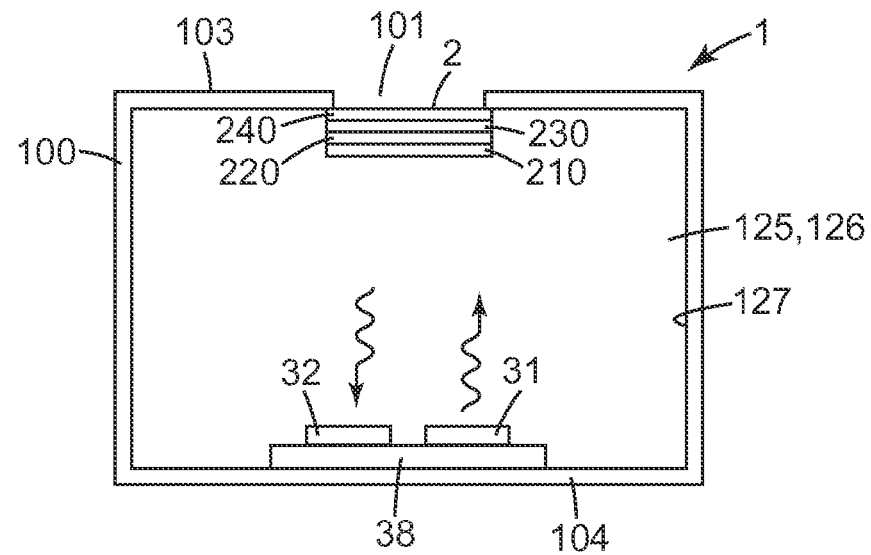
FIG. 5 is a side schematic cross sectional view of an exemplary optoelectronic device.

With reference to FIGS. 4 and 5, device 1 comprises at least one light source 31 for directing light onto the at least one sensing element 2. Light source 31 may comprise any of a variety of light sources, including bulbs (e.g. incandescent bulbs) and the like. In some embodiments, light source 31 may comprise a light-emitting diode (LED). In certain embodiments light source 31 may comprise a source that emits relatively broadband light (e.g., white light). In other embodiments, light source 31 may comprise a narrowband source (e.g., an LED) that emits light in a particular (e.g., relatively narrow) wavelength range. In various embodiments, such narrowband light sources may emit comprise a half-power bandwidth of at most about 50 nm, at most about 40 nm, or at most about 25 nm. Exemplary LEDs that may be used include those available from Optek, Carrollton, Tex., under the designation OVLBx4C7.

With reference to FIGS. 4 and 5, device 1 comprises at least one light detector (photodetector) 32 for measuring reflected light from the at least one sensing element 2. Photodetector 32 may comprise any of a variety of devices capable of measuring the number of incident photons thereon, including for example a photomultiplier tube, a photovoltaic cell, a charge coupled device, and the like. Photodetector 32 may serve to provide a signal (e.g., voltage, current, etc.) that is related to the number of photons detected (e.g., to the intensity or strength of the reflected light received from sensing element 2) and that can be further processed as described later herein. In some embodiments, photodetector 32 may comprise a photodiode. In some embodiments photodetector 32 may detect light of a particular (e.g., relatively narrow) wavelength range. In other embodiments, photodetector 32 may comprise a broadband detector that can detect light over relatively wide wavelengths. In various embodiments, such broadband photodetectors may be able to detect light over a wavelength range of at least about 150 nm wide, 250 nm wide, or 500 nm wide. Exemplary photodetectors that can be used include photodiodes available from OSRAM, Regensburg, Germany, under the designation SFH 2430.

Device 1 thus comprises at least one light source 31 and at least one photodetector 32, configured so as to be able to optically interrogate at least one sensing element 2.

Light source 31 may be positioned such that at least a portion of the light output of source 31 strikes sensing element 2. In some embodiments, light source 31 may be positioned near to sensing element 2 and configured so that light emitted from light source 31 impinges directly on sensing element 2. In various embodiments, light source 31 may be located less than about 30, 20, or 10 mm from sensing element 2. Likewise, photodetector 32 may be positioned near sensing element 2 and configured such that at least a portion of the light reflected by sensing element 2 is received directly by photodetector 32. In various embodiments, photodetector 32 may be located less than about 30, 20, or 10 mm from sensing element 2.

In some embodiments, device 1 may be configured such that light emitted by light source 31 is received by sensing element 2 indirectly, by the use of one or more mirrors (not shown in any figure) in the optical pathway between light source 31 and sensing element 2. Likewise, in some embodiments, device 1 may be configured such that light reflected from sensing element 2 is received by photodetector 32 indirectly, by the use of one or more mirrors (not shown) in the optical pathway between sensing element 2 and photodetector 32.

In various embodiments light source 31 and photodetector 32 may be configured so as to direct at least some light from source 31 onto sensing element 2, and to collect at least some light reflected therefrom by photodetector 32, while minimizing ambient light (or any light other than that directly reflected from sensing element 2) incident upon photodetector 32. In certain embodiments it may be useful to position photodetector 32 adjacent (near) light source 31, as shown in the exemplary design of FIGS. 4 and 5. In various embodiments, photodetector 32 may be positioned at most about 5 mm, 10 mm, or 15 mm from light source 31 (e.g., measured as a center to center distance). In some embodiments, light source 31 and photodetector 32 may be mounted on a common printed circuit board 38, as shown in the exemplary designs of FIGS. 4 and 5. In such cases, light source 31 and photodetector 32 may be in a coplanar configuration, herein defined as a configuration in which at least a portion of light source 31 and of photodetector 32 are in a plane parallel to the plane of the printed circuit board (even though one or both of light source 31 and photodetector 32 may be angled relative to each other, as explained in detail below).

In some embodiments, light source 31, sensing element 2, and/or photodetector 32 may be positioned at defined angles relative to each other so as to enhance the amount of light that is directed from light source 31 onto sensing element 2 and the amount of reflected light from sensing element 2 that is received by photodetector 32.

Figure 6:
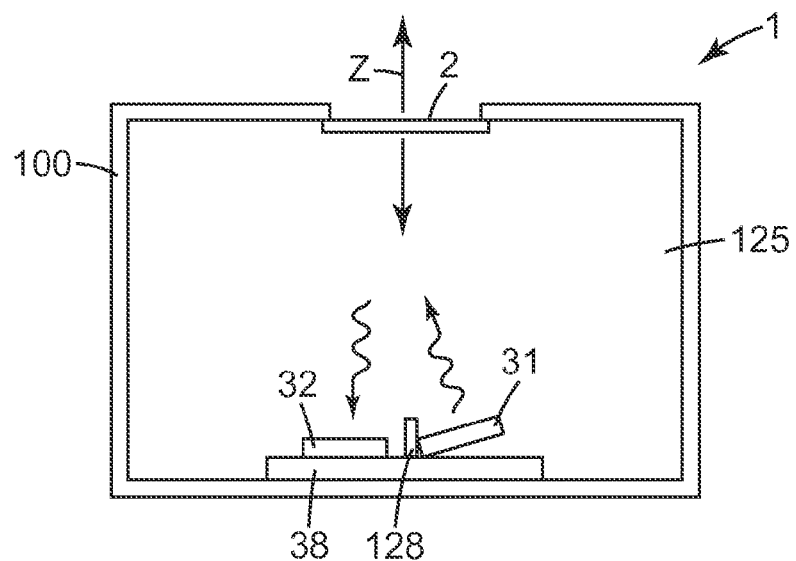
FIG. 6 is a side schematic cross sectional view of an exemplary optoelectronic device.
Figure 7:
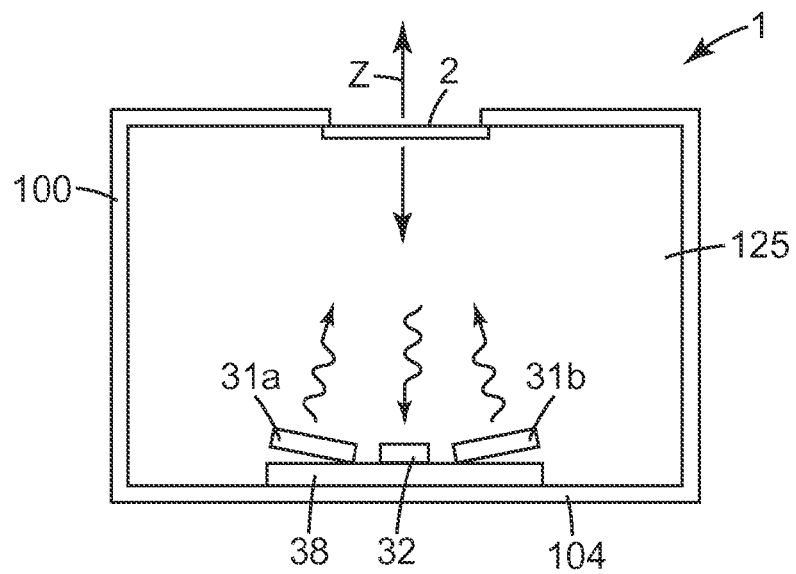
FIG. 7 is a side schematic cross sectional view of an exemplary optoelectronic device.

For example, in designs of the type exemplified in FIG. 7, photodetector 32 is located at the intersection of normal ("z") axis of sensing element 2 with printed circuit board 38 (by which is meant that at least a portion of the light sensitive area of photodetector 32 is located at the intersection of a normal axis of sensing element 2, originating from the center of sensing element 2, with printed circuit board 38), with light source(s) 31 positioned adjacent (laterally beside) photodetector 32 (e.g., slightly off-axis relative to the normal axis of sensing element 2). In such a configuration, light source 31 can be angled so as to enhance the amount of light emitted by light source 31 that is received by sensing element 2. Photodetector 32 is positioned to then receive light reflected by sensing element 2. In various other embodiments, photodetector 32 may (in addition to, or instead of, light source 31) be positioned slightly off axis relative to the normal axis of sensing element 2. Any suitable relationship between light source 31, sensing element 2, and photodetector 32 is acceptable as long as sufficient ability to perform the optical interrogation of sensing element 2 is provided. For example, rather than being positioned adjacent to, and relatively parallel to, major surface 103 of housing 100 (as shown in FIGS. 4, 5, and 6), sensing element 2 may be positioned at a distance from and/or at an angle thereto, as long as the proper relationship of sensing element 2 to light source 31 and photodetector 32 is provided.

In specific embodiments, light source 31 can be mounted on (e.g., attached to) printed circuit board 38 at an angle relative to printed circuit board 38 (as shown in FIG. 6), so as to establish the desired angle between light source 31 and sensing element 2. For example, if light source 31 is a light-emitting diode it may be electrically connected to printed circuit board 38 via any well known mounting method. Through-hole methods may be better able to establish the desired angle, although surface mount methods may be used if desired. If desired, one or more positioning devices (e.g., holders, collars, etc.) may be used to position light source 31 on printed circuit board 38 at the desired angle. In various additional embodiments (not shown in FIG. 6), photodetector 32 can be mounted on (e.g., attached to) printed circuit board 38 at an angle relative to printed circuit board 38, in similar manner as done for light source 31.

Device 1 may be designed so as to enhance the amount of light received by photodetector 32 that is directly reflected from sensing element 2, while minimizing light received by photodetector 32 from other sources. For example, example, certain designs of device 1 can minimize the amount of ambient light that enters interior space 125 and can minimize the amount of light that may be transmitted directly from light source 31 to photodetector 32.

Thus, in some embodiments some, most or all of housing 100 may be made of an opaque material. In some embodiments some, most, or all of interior surfaces 127 of housing 100 (e.g., the surfaces facing interior space 125) may be nonreflective (e.g., light-absorptive, opaque, black, etc.). This may be achieved for example by molding housing 100 of a pigmented (e.g., opaque) material, by the use of an antireflective, opaque, etc. coating on the interior surfaces of housing 100, and the like. In some embodiments, light source 31 may comprise a source (e.g., an LED) that emits light in a relatively narrow beam angle. In various embodiments, light source 31 may comprise a beam angle such that more than 90% of the light is emitted within an angle of plus or minus 30 degrees from the center of the beam, or within an angle of plus or minus 20 degrees from the center of the beam. In some embodiments, one or more optical barriers may be positioned to intercept light that otherwise might travel directly from light source 31 to photodetector 32. For example in the exemplary design of FIG. 6 is shown optical barrier 128 that is positioned to block at least some light from reaching photodetector 32. Optical barrier 128 may be comprised of any suitable material (e.g., an opaque material) and may be any suitable size or shape and placed in any suitable location, as long as it achieves the desired blockage of light. Optical barrier 128 may be positioned near light source 31. In some embodiments, optical barrier 128 may comprise a holder (e.g., a collar) that assists in holding light source 31 in a desired configuration (e.g. angle) with respect to printed circuit board 38. In addition to, or instead of, this arrangement, an optical barrier may be likewise positioned near photodetector 32 for similar purposes.

In further embodiments, multiple light sources 31 and/or multiple photodetectors 32 may be used in device 1. Many variations on this approach are possible. For example, two, three, four, or more light sources 31 may be used. In specific embodiments, different light sources 31a, 31b, etc., each emitting light with a different peak wavelength than that emitted by the other light sources (for example, LED's with different emission wavelength ranges) may be used. In such a design, the different light sources may be mounted adjacent to common photodetector (an exemplary design involving two light sources 31a and 31b is shown in FIG. 7). Each individual light source can be positioned off-axis with respect to sensing element 2, and/or angled with respect to printed circuit board 38, as previously described with respect to light source 31 (e.g., as shown in exemplary manner in FIG. 7). One or more optical barriers 128 may be present.

In further embodiments, multiple photodetectors can be used. For example, each light source 31 that emits light with a particular peak wavelength can be used in combination with a photodetector designed to detect light in that particular wavelength range. In other embodiments, multiple (e.g., narrowband) photodetectors can be used in combination with a single broadband light source 31.

In other embodiments, a single photodetector 32 (e.g., a broadband detector 32 capable of detecting light of the wavelength range emitted by each of separate, individual narrowband light sources 31) can be used in combination with multiple narrowband light sources 31 (e.g. as shown in FIG. 7). In such designs, light sources 31 can be operated sequentially with sufficient time delay (e.g., at least 1 millisecond) in between the triggering of each light source 31 such that common photodetector 32 can detect a signal corresponding to light emitted from light source 31a, can then separately detect a signal corresponding to light emitted from light source 31b, and so on. Such a design may have advantages in only requiring one photodetector.

The use of multiple light sources 31 and/or multiple photodetectors 32 may allow enhanced operation of device 1. For example such designs may allow the detection of a wider range of detectable analytes, may allow a wider concentration range of analyte to be detected, may allow more precise quantitation of the concentration of analyte, may negate the need to calibrate device 1 each time that a new or replacement sensing element 2 is installed, and so on. Thus in some embodiments, performance of the methods described herein does not require that the sensing element is exposed to a calibration gas containing a known non-zero concentration of analyte, prior to the monitoring of an atmosphere potentially containing the analyte.

The devices and methods disclosed herein may also enhanced interrogation of sensing element 2 via optical reflectance, with minimum use of space and with minimum expense, since they minimize the use of components such as fiber optic cables, lens arrays, filter wheels, and the like. In particular, devices and methods disclosed herein allow the production of device 1 that is lightweight, portable, and may function without an external power source if desired. In various embodiments, interior space 125/126 of device 1 may be less than about 100 $cm^3$, less than about 60 $cm^3$, or less than about 30 $cm^3$.

In some embodiments, methods described herein may enable sensing element 2 to function as an end of service life indicator (ESLI) in connection with respiratory protection devices. Various exemplary respiratory protection devices are described in US Published Patent Application 2008/0063575, titled ORGANIC VAPOR SORBENT PROTECTIVE DEVICE WITH THIN-FILM INDICATOR, which is incorporated by reference herein for this purpose. In such embodiments, certain components (e.g., cap 140, protective layer 300) that may find use when device 1 is used as a badge or area monitor, may or may not be present.

Figure 8:
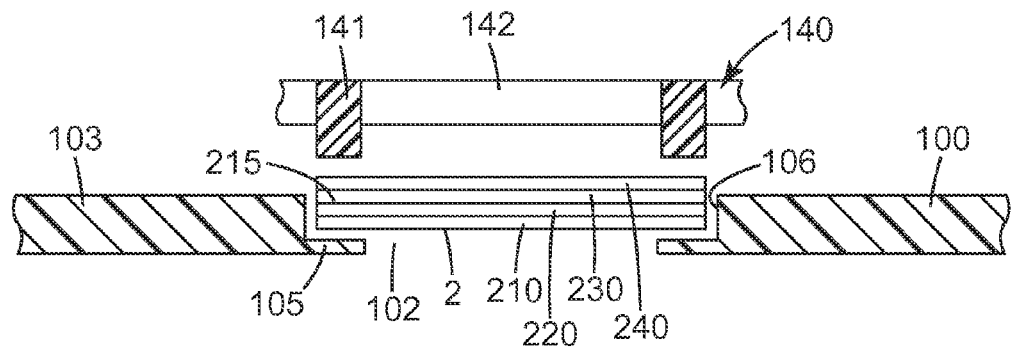
FIG. 8 is a partially exploded side cross sectional view of a portion of an exemplary optoelectronic device comprising an exemplary sensing element.

In some embodiments, sensing element 2 may be provided as a permanently installed component of device 1. In other embodiments, sensing element 2 may be a disposable (e.g., removable and/or replaceable) component. It may be advantageous to securely position (e.g., attach) sensing element 2 in place in device 1 (and optionally, to occlude opening 102 in so doing), with minimal use, or no use, of adhesives (including for example pressure sensitive adhesives, liquid adhesives, thermally curable adhesives, radiation curable adhesives) that may contain small molecules that might interfere with the functioning of sensing element 2. Thus, it may be advantageous to hold sensing element 2 in place via one or more mechanical attachment means (e.g., a clip, clamp, cap, or the like). It may also be advantageous to hold sensing element in place in such a manner as does not cause sensing element 2 to deflect, bow or deform. In embodiments of the type shown in an exemplary manner in FIG. 8, sensing element 2 is held in place (and is caused to occlude opening 102) by use of cap 140. In such embodiments, housing 100 may comprise flange 105, upon which perimeter edge portion 215 of sensing element 2 (e.g., a portion of substrate 210 of sensing element 2) may rest, and wall 106, that restricts sensing element 2 from moving laterally relative to opening 102. Cap 140 is attachable to housing 100 of device 1 and, when attached, securely holds sensing element 2 in place so as to occlude opening 102. Cap 140 may be attachable to housing 100 of device 1 by any suitable attachment mechanism (not shown in any Figure). Cap 140 may thus comprise a screw-on connection mechanism, a bayonet-style connection mechanism, may attach via one ore more clips, clamps and the like, may attach by the use of mechanical fasteners such as hook and loop fasteners, elastic bands, and so on. Cap 140 may comprise portion 141 that is designed to securely hold perimeter edge portion 215 of sensing element 2 in place (e.g., against flange 105 of housing 100). One or more sealing gaskets (e.g., O-rings) may be used (e.g., in between edge portion 215 of sensing element 2 and portion 141 of cap 140 or flange 105 of housing 100) to assist in achieving occlusion of opening 102. Cap 140 may also comprise analyte-permeable portion 142. Portion 142 may comprise an open space (e.g., as in the exemplary embodiment of FIG. 8). Or, it may comprise one or more members (e.g., louvers, rails) with spaces therebetween and/or may comprise perforated sheeting, mesh, etc. (e.g., as in the exemplary embodiment of FIG. 9), so as to provide mechanical protection to sensing element 2 while still permitting analyte to reach sensing element 2. While in embodiments of the type shown in FIGS. 8 and 9 sensing element 2 is held in place by being pressed inward (toward interior space 126 of device 1), in other embodiments sensing element 2 may be held in place by being pressed outwards, e.g., against a flange or some other portion of housing 100.

However achieved, when sensing element 2 is securely held in place opening 102 may be occluded such that interior space 125 becomes a sealed interior space (126). By sealed is meant that vapor or solids (e.g., dust) cannot penetrate into interior space 126 of device 1. The occluding of opening 102 may be provided by sensing element 2 (e.g., by virtue of optically clear substrate 210 of sensing element 2 being may be impermeable to analyte and/or to any other gas, liquid, vapor, etc.); or, the occluding of opening 102 may be provided by one or more secondary barrier layers. Such a secondary barrier layer may be associated with sensing element 2 (e.g., adhered to sensing element 2, provided along with sensing element 2 in a kit, etc.), or may be a permanently installed component (e.g., a transparent window) of housing 100 of device 1.

In designs of this type, analyte-permeable reflective layer 240 of sensing element 2 may face outward (away from sealed interior space 126), and optically clear substrate 210 of sensing element 2 may face inward so that sensing element 2 can be optically interrogated by way of light rays 40 and light rays 41 and 42 passing through optically clear substrate 210. In such designs, device 1 may be capable of detecting an analyte, without the analyte (or any other solid, liquid or vapor material) entering sealed interior space 126. Since interior space 125 contains various optoelectronic components which may be deleteriously affected by the analyte and/or by other substances, providing interior space 125 as a sealed interior space (126) may have advantages. In addition to protecting optoelectronic components within interior space 126 from substances outside device 1, impermeable substrate 210 (and/or any secondary barrier layers present) may protect sensing element 2 from being adversely affected by substances that may be present within interior space 126 (e.g., adhesives or substances therein, that may have been used in the assembly of the optoelectronic components).

Cap 140 may also be used in embodiments of the type shown in FIG. 4, e.g. to cover non-occluded opening 101 in such a manner to prevent physical damage to the various components within interior space 125, while still providing for access of analyte into interior space 125.

Other layers, components, etc. may also be provided in device 1 for various purposes. For example, one or more additional layers (e.g., optically clear films) may be provided between sensing element 2, and light source(s), photodetector(s) 32, and/or various other optoelectronic components of device 1. In some embodiments, light source(s) 31, photodetector(s) 32 and/or various other optoelectronic components may be present in interior space 125 of device 1 behind one or more optically clear layers which may protect such components (e.g., from dust, dirt, contamination, etc.) while still allowing light to pass through the optically clear layer for the interrogation of sensing element 2.

In some embodiments, it may be desirable to provide one or more layers which are permeable to analyte in the vapor or gas phase, but which provide protection against the passage of liquid analyte, or of any liquid or solid substance that might interfere with the operation of device 1, into interior space 125 of device 1. Thus, it may be useful to provide a protective layer 300 positioned between opening 101/102 and interior space 125/126 of device 1. Protective layer 300 may comprise any material that is sufficiently (gas and/or vapor)-permeable so as to allow sufficient passage of a gas and/or vapor phase analyte to assure adequate response of sensing element 2, while substantially or completely preventing the passage of undesired liquid-phase materials. Thus, protective layer 300 may comprise any suitable porous material that allows passage of gas and/or vapor while substantially preventing passage of liquid. (In this context, substantially preventing passage of liquid means that while the protective layer might allow liquid to penetrate through the material upon the application of sufficiently high pressure as might be achieved by e.g. pumping, liquid will not penetrate through the layer in such events as incidental contact, pouring, splashing, etc.). Such materials may include for example porous and/or microporous membranes, nonwoven webs, woven fabrics, and the like. Such materials may be treated if desired so as to modify their wettability and/or their ability to prevent the passage of liquid. Exemplary materials that may be used for protective layer 300 include e.g. materials available from Pall Corporation, of East Hills, N.Y. under the trade designation Versapore R.

Figure 9:
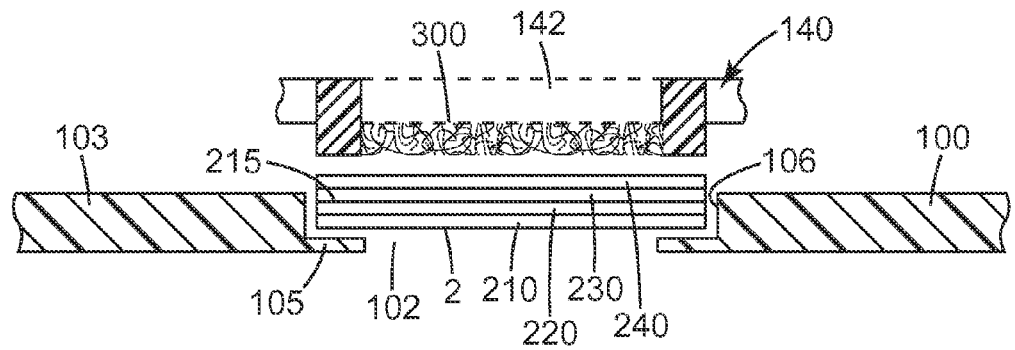
FIG. 9 is a partially exploded side cross sectional view of a portion of an exemplary optoelectronic device comprising an exemplary sensing element and an exemplary protective layer.

Protective layer 300 may be placed within or near opening 101/102, and may be held in place for example by cap 140, as pictured in the exemplary configuration is shown in FIG. 9. In some embodiments, protective layer 300 may comprise a compressible porous material that, when cap 140 is attached to housing 100 of device 1, assists in holding sensing element 2 in place.

Protective layer 300 may or may not be in direct contact with sensing element 2 (e.g., with analyte-permeable reflective layer 240 of sensing element 2), as long as the desired protection is required. Protective layer 300 may be positioned within a recess in cap 140, e.g. adjacent analyte-permeable portion 142 of cap 140, which may reside above protective layer 300 to hold it in place and provide mechanical protection, while still permitting analyte to reach sensing element 2. Protective layer 300 and/or cap 140 may be replaceable if desired.

Upon interrogation of sensing element 2 using methods and devices disclosed herein, a signal may be obtained that is related to the presence and/or concentration of an analyte of interest (e.g., in an atmosphere that is monitored). In some embodiments, the signal generated by the at least one photodetector 32 of device 1 is an electrical signal, e.g., in the form of a voltage or current (for example, as generated by photodetector 32 in response to light incident on photodetector 32). That is, photodetector 32 may convert an optical signal (e.g., light intensity) from sensing element 2 to a signal such as voltage, that can then be manipulated, processed, etc. Device 1 can further comprise one or more analog to digital converters that can provide the signal in a digital form for ease of processing by a microcontroller. In the case of multiple photodetectors 32, a separate signal may be provided by each photodetector 32.

Figure 10:
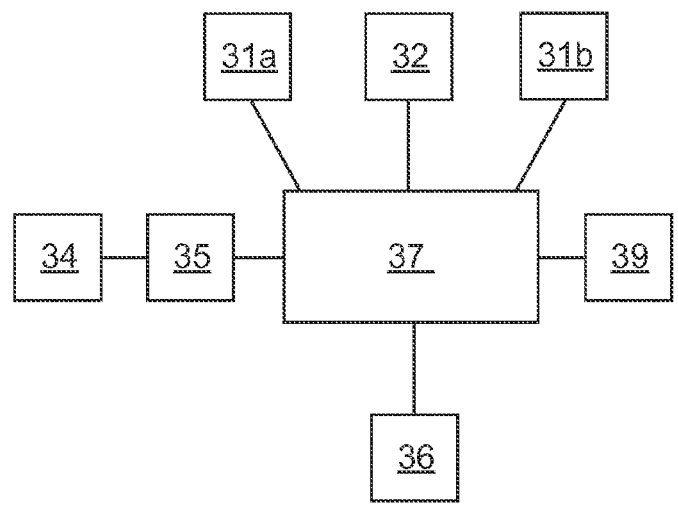
FIG. 10 is a block diagram illustrating the functioning of an exemplary optoelectronic device.

The signals received from the one or more photodetectors 32 can be mathematically manipulated (individually or in combination) according to algorithms resident in the circuitry of device 1 (e.g., loaded into software or firmware) as desired. Thus, device 1 may comprise such components, circuitry, etc., as needed to perform such desired signal processing, and also as needed to control light sources 31 and/or photodetectors 32, and so on. With reference to the block diagram of FIG. 10, device 1 may comprise microcontroller 37 that may operate light source(s) 31 and operate (and receive signals from) photodetector(s) 32, may process, manipulate, etc., signals received from photodetector(s) 32, may hold various data and parameters in memory, may operate display 36 and communicate with user interface 39, may receive power from (internal or external) power source 34 via power supply 35, and may carry out other functions as needed. In particular embodiments, device 1 can comprise the type of microcontroller exemplified by the product available from Texas Instruments under the trade designation MSP430F437IPN, which may be particularly suited for the uses described herein. Device 1 may comprise other electronic and/or optical components as needed to carry out the functioning of device 1. Such components may include, but are not limited to, one or more resistors, capacitors, inductors, integrated circuits, drivers, transceivers, antennas, etc. The various components of device 1 can be connected to, and/or physically mounted on, one or more printed circuit boards. In some embodiments, the various components of device 1 are mounted on a single, common circuit board 38.

In summary, device 1 can, from signals received and/or processed as described herein, produce a notification signal that is associated with, e.g. representative of, a concentration value of an analyte of interest in a monitored atmosphere. The notification signal can be communicated to a user of device 1 (for example, by a visual, audio, or tactile signal). In one embodiment, the notification signal can be an actual numerical value of the concentration of the analyte in the monitored atmosphere. In addition to this, and/or instead of this, and notification signal can be provided that, while not a numerical value, is associated with such a numerical value. For example, device 1 may provide an auditory signal (e.g., a beep, chirp, alarm signal), a visual signal, and/or a vibrational signal, upon the detection of the analyte, and/or of the detection of a certain amount of the analyte.

In some embodiments, device 1 may provide nonquantitative indications, (for example, indicating whether an analyte of interest is present, e.g., above a certain concentration). In some embodiments, device 1 may provide semiquantitative and/or quantitative information (e.g., an estimate or indication of the concentration of the analyte in the air that is being monitored). In some embodiments, device 1 may provide a cumulative indication (that is, an integrated indication that arises from the concentration of analyte in the monitored air over a period of time that may range up to a few hours). In some other embodiments, device 1 may provide "real time" readings that arise from the instantaneous (e.g., over a period of a few minutes or less) concentration of analyte in the air. In some embodiments, device 1 may communicate, either in real time or periodically (e.g. by transmission of datalogged information), such information to a receiving station. For example, device 1 may transmit such information (e.g., by wireless or infrared transmission) to a computer, workstation, central processing facility, or the like.

Device 1 may be used to detect and/or monitor one or more analytes of interest. Such an analyte may comprise a vapor or gas that may be present in an environment (often, an air atmosphere) that is desired to be monitored. In some embodiments, the analyte is an organic vapor (e.g., a volatile organic compound). Representative organic analytes may include substituted or unsubstituted carbon compounds including alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, toluene, styrene, xylenes, methyl chloroform, tetrahydrofuran, methanol, ethanol, iso-propyl alcohol, n-butyl alcohol, t-butyl alcohol, 2-ethoxy-ethanol, acetic acid, 2-aminopyridine, ethylene glycol monomethyl ether, toluene-2,4-diisocyanate, nitromethane, acetonitrile, and the like.

Device 1 may optically interrogate sensing element 2 by emitting light from at least one light source 31, directing at least a portion of the emitted light onto at least one sensing element 2, and measuring the amount of light reflected from sensing element 2 via use of at least one photodetector 32. The characteristics of the light reflected from sensing element 2 will result from the interference of light that is reflected from various layers (e.g. reflective and/or semireflective layers) and/or interfaces of sensing element 2. Such reflected light may have a reflectance spectrum of the general type shown in generic representation in FIG. 11, with one or more peaks (e.g., 181, 182, and/or 183, etc.) and valleys over a given wavelength range. The size and/or position of the peaks may change in response to the presence of an analyte.

Rather than attempting to interrogate the entire reflection spectrum as might be done with complex instrumentation, it may be preferable to selectively interrogate sensing element 2 at one or more specific wavelength ranges. Thus in some embodiments device 1 comprises one light source 31 that is designed to emit light in predetermined, relatively narrow wavelength range A (with reference to FIG. 11). The boundaries of wavelength range A may or may not be sharp or absolute cutoffs, depending on the characteristics of the particular light source and/or detector used. Upon a shift in the position or size of peak 182 (i.e., due to a change in the concentration of an analyte), the amount or intensity of reflected light that is detected by photodetector 32 may change.

In some embodiments, wavelength range A may be chosen such that for a given design of sensing element 2, wavelength range A falls at or near the maximum 184 of a peak 182 (e.g., a major or primary peak) in the reflection spectrum of sensing element 2 in the absence of analyte. In such a configuration, the directing of light of wavelength range A onto sensing element 2 may result in a relatively large change in the light reflected by sensing element 2 and detected by photodetector 32, upon a shift in the size or position of peak 182 in response to a change in the amount of an analyte. Thus, such methods may enhance the responsiveness of device 1 to the presence and/or concentration of an analyte. The specific wavelength range chosen may depend upon the properties of the particular sensing element 2 that is used, the particular analyte(s) that is desired to be monitored, etc. In various embodiments, the center of the wavelength range may be within about 10 nm, 20 nm, or 40 nm of a peak maximum. In specific embodiments, it may be preferable to interrogate sensing element 2 in a wavelength range centered around approximately 520 nm, or a range centered around approximately around 640 nm.

In certain embodiments described above, interrogation at a given predetermined wavelength range is achieved by the use of a narrowband light source 31. In such case photodetector 32 may be narrowband or broadband as desired. Alternatively, narrowband photodetector 32 may be used, in which case light source 31 may be narrowband or broadband as desired.

Figure 11:
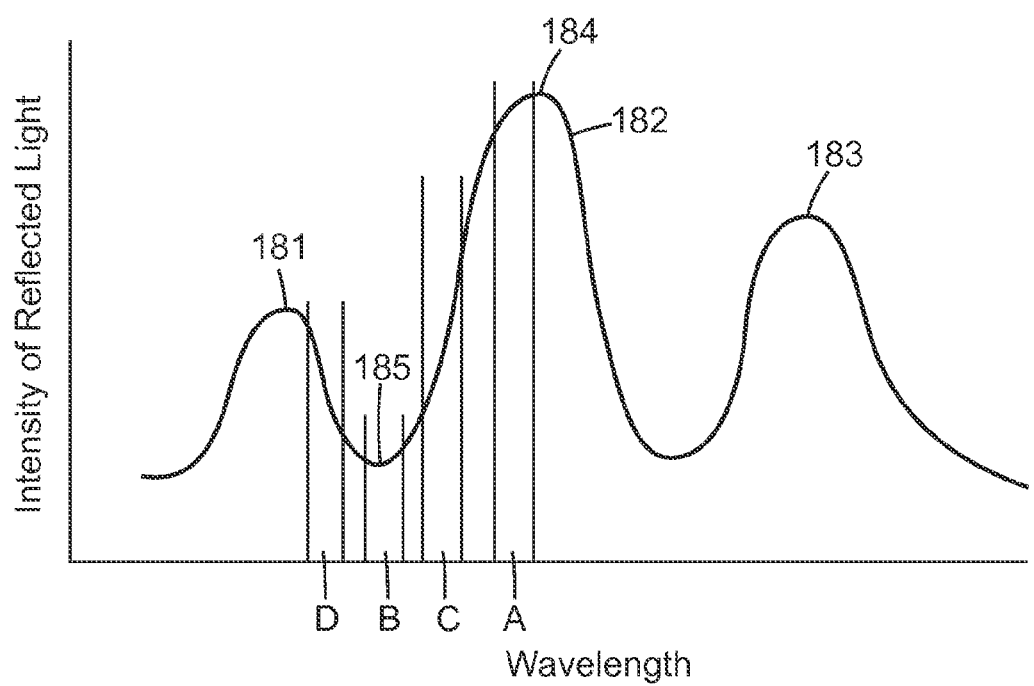
FIG. 11 is a generic representation of a reflection spectrum of an exemplary sensing element.

In some embodiments, reflected light from sensing element 2 is monitored at least at two different wavelength ranges A and B (with reference to FIG. 11). This may be achieved for example by the use of an additional light source 31 and/or photodetector 32. In particular embodiments, this may be done by use of two or more separate, narrowband light sources 31a and 31b, as depicted in the exemplary design of FIG. 7. In such case a single (e.g., broadband) photodetector may be used, also as shown in FIG. 7, with the signals at the different wavelength ranges being obtained by temporally spacing (i.e., staggering in time) the light emitted by light source 31a and 31b so that reflected light resulting therefrom can be separately detected by photodetector 32. Other approaches may also be used. In some embodiments, a broadband light source 31 can be used, in combination with narrowband photodetectors that are capable of distinguishing light in wavelength range A from light in wavelength range B.

However accomplished, the monitoring of light reflected from sensing element 2 in multiple wavelength ranges may provide significant advantages. In particular embodiments, wavelength range A may be chosen to fall at or near the maximum 184 of a peak 182 in the reflection spectrum of sensing element 2 in the absence of analyte, as described above. Wavelength range B may be at least somewhat removed from wavelength range A, and in some embodiments may be at or near a valley minimum 185 in the reflection spectrum of sensing element 2 in the absence of analyte. In particular embodiments, wavelength B falls at or near valley minimum 185 that is immediately adjacent to peak 182 of which wavelength λ is monitored (as shown in FIG. 11).

In such configurations, a signal from photodetector 32 indicative of the amount of light detected in wavelength range A can be compared (e.g. ratioed, by microprocessor 37 of device 1), to a signal from photodetector 32 indicative of the amount of light detected in wavelength range B. Such comparison/ratioing may provide significant advantages. For example, it may allow the confirmation that a new or replacement sensing element 2 is in operating condition (e.g., has not been prematurely exposed to analyte, damaged, etc.). Thus in some embodiments, methods disclosed herein include the step of obtaining an initial compared signal with the sensing element exposed to an atmosphere free of analyte (e.g., containing less than 1 ppm analyte) and determining whether the initial compared signal is in an acceptable range. Such use of compared (e.g., ratioed) signals may also enhance the dynamic range of device 1. In the context of the methods disclosed herein, the comparing of first and second signals (e.g., signals indicative of an amount of light detected in a first wavelength range and a second wavelength range) can include the comparing of averaged signals (e.g., the obtaining of multiple first signals and averaging them and the obtaining of multiple second signals and averaging them, and comparing the averaged first signal with an averaged second signal), as well as the comparing of an individual first signal with an individual second signal.

The specific wavelength ranges chosen may depend upon the properties of the particular sensing element 2 that is used, the particular analyte(s) that is desired to be monitored, etc. In various embodiments, wavelength range A and wavelength range B are chosen such that their centerpoints are at least 20, at least 40, or at least 60 nanometers apart. In further specific embodiments, wavelength range A and wavelength range B are chosen such that their centerpoints are at most 140, at most 120, or at most 100 nm apart. In various embodiments, the center of the first wavelength range may be within about 10 nm, 20 nm, or 40 nm of a peak maximum, and the center of the second wavelength range may be within about 10 nm, 20 nm, or 40 nm of a valley minimum. In further specific embodiments, optical interrogation is performed wherein wavelength range A is centered around approximately 520 nm, and wherein wavelength range B is centered around approximately 640 nm. As mentioned, interrogation in wavelength ranges A and B may be achieved e.g. by use of narrowband light sources such as LEDs and the like. There may be some overlap in the wavelength of the light emitted by the different light sources; however, this may not detract from the successful interrogation of sensing element 2 as long as sufficient differences in the signals obtained therefrom are available.

If desired, additional optical interrogation may be performed at other wavelength ranges, e.g., those marked C and D in FIG. 11. Such additional ranges may be in between ranges A and B (as in range C), or outside ranges A and B (as in range D). Such additional optical interrogation ranges (which may be provided e.g. by the use of additional light sources 31 and/or photodetectors 32) may provide enhanced resolution, dynamic range, precision, and the like. Signals obtained in these wavelength ranges may be compared (e.g., ratioed) to signals at other wavelength ranges, as described above.

Innovative use of the signal processing capabilities of device 1 (e.g., carried out by microprocessor 37) may provide additional advantages. For example, the signals collected from photodetector 32 may be held resident in memory (e.g., of microprocessor 37) so that the time-dependent history of the signals may be accessed and consulted. This may be useful, for example, in a case in which (e.g. in the presence of a certain amount of analyte) a second peak (e.g., peak 181) shifts sufficiently close to the A wavelength range that a signal is received in the A wavelength range resulting from peak 181 that is similar to that initially received from a first peak (e.g. peak 182) in the absence of analyte. By following the time-dependent history of the signals received from photodetector 32 (e.g., the signal in wavelength range A falling, then rising again towards its initial value) device 1 might be able to distinguish such a condition (e.g., perhaps caused by a very large amount of analyte) from a condition in which a relatively constant reflected light signal (e.g., resulting from peak 182) is received over the time period of the potential analyte exposure. Similar signal processing may be performed when using compared (e.g., ratioed) signals.

Enhanced performance of device 1 may require that sensing element 2 be interrogated at a sampling rate sufficiently faster than the expected rate of response of the reflectance properties of sensing element 2 to an analyte. However, it may not be advantageous, e.g., for purposes of power consumption, to monitor sensing element 2 continuously. In various embodiments, sensing element 2 is interrogated at a frequency of at least 6 interrogations per minute, at least 60 interrogations per minute, at least 120 interrogations per minute, or at least 240 interrogations per minute.

Other information may be held resident in memory of microprocessor 37 to provide enhanced functioning of device 1. For example, information (e.g., a predetermined response curve, empirically obtained via exposure of a sensing element to known analyte concentrations) may be provided that relates a signal (e.g., the intensity of light at wavelength range A); or, a compared signal (e.g. the ratio of the intensity of light at wavelength range A to that at wavelength range B), etc., to a concentration of analyte in a monitored atmosphere. Device 1 can thus function by correlating a compared signal to a predetermined response curve so as to obtain a concentration value that is associated with, or representative of, the concentration of an analyte in a monitored atmosphere. A single response curve may be preloaded (e.g., permanently) into the memory of device 1; or, response curves may be uploaded periodically into the memory of device 1 for use with particular designs of sensing element 2, particular analytes, and so on. Multiple response curves may be used. In the context of the methods disclosed herein, such correlating of a compared signal with a response curve encompasses the correlating of an averaged compared signal (e.g., resulting from the obtaining of multiple compared signals and averaging them), as well as the correlating of an individual compared signal.

EXAMPLE

A 3M Model 110 Carbon Monoxide Monitor from 3M Company, St. Paul Minn. was disassembled and the electronic components removed therefrom with the exception of the liquid crystal display. A printed circuit board was designed of the proper size, and bearing suitable connections, so as to fit into the housing of the 110 Monitor and to interface with the LCD display via zebra strip connections. The printed circuit board was custom designed to receive, support, and electrically connect, the various components discussed hereafter.

Upon the printed circuit board were mounted a photodiode (SFH 2430, OSRAM, Regensburg, Germany). The printed circuit board and the location of the photodiode were chosen so that when the printed circuit board was secured in the 110 housing, a sensing element was placed in the opening of the 110 housing, and the two halves of the housing were fitted together, the photodiode was facing the sensing element and positioned in alignment with the normal axis of the sensing element (in similar manner to the design shown in FIG. 7).

Upon the printed circuit board were mounted two LEDs. The first was a green LED (OVLBG4C7, Optek, Carrollton, Tex.) with a peak wavelength of emitted light centered at approximately 520 nm; the second was a red LED (OVLBR4C7, Optek) with a peak wavelength of emitted light centered at approximately 640 nm. The LEDs were mounted in positions flanking the photodiode (in similar manner to that shown in FIG. 7) with each LED spaced approximately 7 mm from the photodiode (measured center to center). The LEDs were mounted to the printed circuit board via through-hole connections, with the connecting wires being bent slightly so that each LED was angled slightly toward the photodiode in similar manner to that shown in FIG. 7. The angle was calculated so that when a sensing element was placed in the opening of the 110 housing, and the two halves of the housing were fitted together, each LED would emit light toward the central area of the sensing element. An LED collar-style holder (attached to the printed circuit board via screws) was used to assist in holding each LED in the proper position and angle. The LED holders were made of opaque (black) plastic and the portion of the collar that was between each respective LED and the photodiode served to minimize the amount of light that could travel directly to the photodiode from that LED.

Other components were mounted to the printed circuit board, including an SPI Bus Serial FRAM (FM25H20-DG, Ramtron), a low noise CMOS (AD8603AUJZ, Analog Devices), 600 mA Step-Up DC/DC (LTC3429ES6, Linear Technology), 50 mA ultra low power LDO (TPS79730DCKR, Texas Instruments), 16-bit Flash/RAM A/D/120 seg LCD (MSP430F437IPN, Texas Instruments), a single chip 2.4 Hz transceiver (nRF24LO1+, Nordic Semiconductor), and a 2.4 HGz chip antenna (RFD58005, RFD). Other items as needed to operate the circuitry and various components thereof were also provided on and/or mounted to the printed circuit board, including various resistors, capacitors, inductors, and the like, as is well known in the art. A 3.6 V lithium battery was hardwired to the printed circuit board.

The monitor housing was then reassembled including the printed circuit board and above-described components. Various information and algorithms as needed to operate the device, drive the LEDs, process signals received from the photodiode, etc., was uploaded into the firmware and/or software memory of the device. Specifically, algorithms were uploaded according to which the device could sequentially operate the red and green LEDs and monitor a reflected light signal corresponding to operation of each LED. The algorithms were configured such that each LED was triggered at a frequency of approximately once per second, with a timing pattern as follows: red LED on—2 mS (millisecond); measure and process resulting reflected light signal—2 mS; pause—990 mS; green LED on—2 mS, measure and process resulting reflected light signal—2 mS; pause 2 mS. Further algorithms were uploaded allowing the device to calculate, for each triggering of the red and green LEDs and resulting reception of reflected light by the photodiode, the ratio of the light reflected from the sensing element in response to light emitted from the green LED, to light reflected from the sensing element in response to light emitted from the red LED. Also uploaded was a response curve (which in this case was an arbitrary curve, for purposes of demonstration, rather than being obtained from exposure of a sensing element to known analyte concentrations) relating an amount of analyte in a monitored atmosphere, to a ratio of light reflected at the various wavelengths.

The result was a functional optoelectronic device comprising an operating circuit capable of driving the LEDs so as to emit light, of operating the photodiode so as to receive light signals, of interfacing with a user so as to upload information as described above, of calculating a concentration of analyte in a monitored atmosphere based on the ratio of light signals at the different wavelengths in combination with a provided response curve, and of presenting a notification signal representative of a concentration of analyte in a monitored atmosphere (e.g., a reading in parts per million) on the LCD display screen of the device.

The louvered front cover (that covered an opening into the interior of the 110 device) was removed. An annular housing (designed to fit into the opening in the housing and comprising an annular flange) was made via stereolithography (SLA) and was attached to the opening in the housing.

A sensing element similar to the type described in US Published Patent Application 2008/0063874 was prepared via methods similar to those described in Examples 1-6 of that patent application, except that the sensing element comprised a clear polymeric substrate (polyester) rather than a glass substrate. The sensing element was approximately 16 mm in diameter. The sensing element was placed into the opening of the housing of the monitor containing the above-described optoelectronic system, whereupon the perimeter edge of the sensing element rested against the annular flange of the SLA housing. The analyte-permeable reflective surface of the sensing element faced outward, with the optically transparent substrate of the sensing element facing inward toward the interior space of the monitor. A polymeric cap (designed to attach via bayonet connection to the SLA housing, and containing a louvered center portion) was attached to the SLA housing of the 110 monitor, holding the sensing element securely in place.

An analyte exposure system was constructed comprising a primary chamber connected by two conduits to a secondary chamber to which liquid analyte could be inputted. The secondary chamber contained a heating element to volatilize the liquid analyte. A fan was provided to circulate air through the primary/secondary chamber closed loop system so that a relatively constant level of analyte could be established and maintained in the primary chamber. A photoionization detector was provided so as to monitor the approximate amount of airborne analyte present in the system at any given time. Analyte levels could be increased by addition of liquid analyte to the secondary chamber exposure and decreased by bleeding air into the system.

The optoelectronic device was powered up and inserted in the primary chamber of the analyte exposure system and allowed to stabilize in a recirculating acetone-free air environment. Liquid acetone was then added to the secondary chamber sufficient to bring the concentration of acetone in the recirculating atmosphere to approximately 100 ppm (as measured by the photoionization detector). After a period of time, additional acetone was added to bring the concentration of acetone to approximately 275 ppm. After a period of time, additional acetone was added to bring the concentration of acetone to approximately 500 ppm. After a period of time, bleed air was introduced to reduce the concentration of acetone down to a negligible level.

Figure 12:
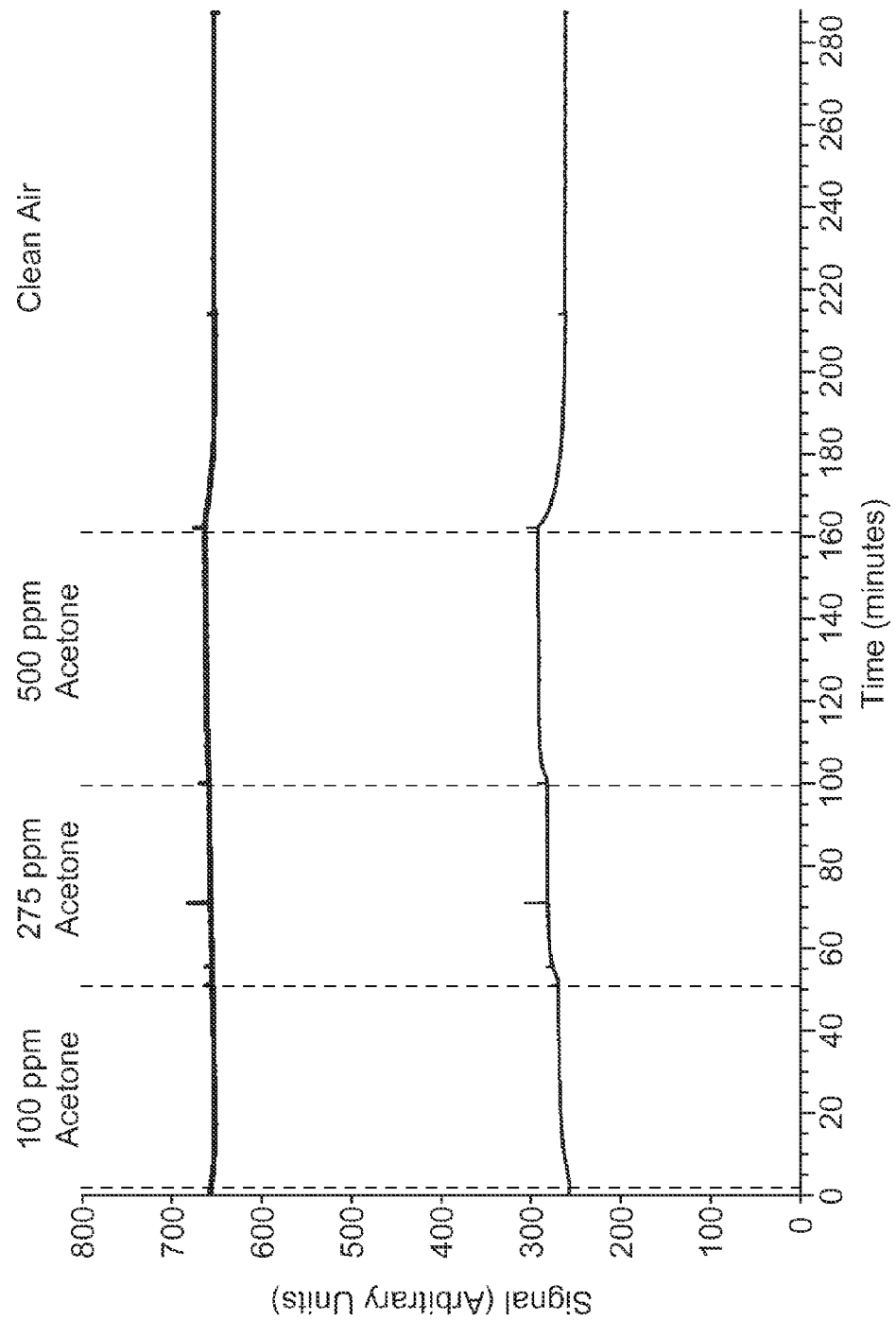
FIG. 12 shows optical reflectance data in response to an analyte, obtained by an exemplary optoelectronic device.
Figure 13:
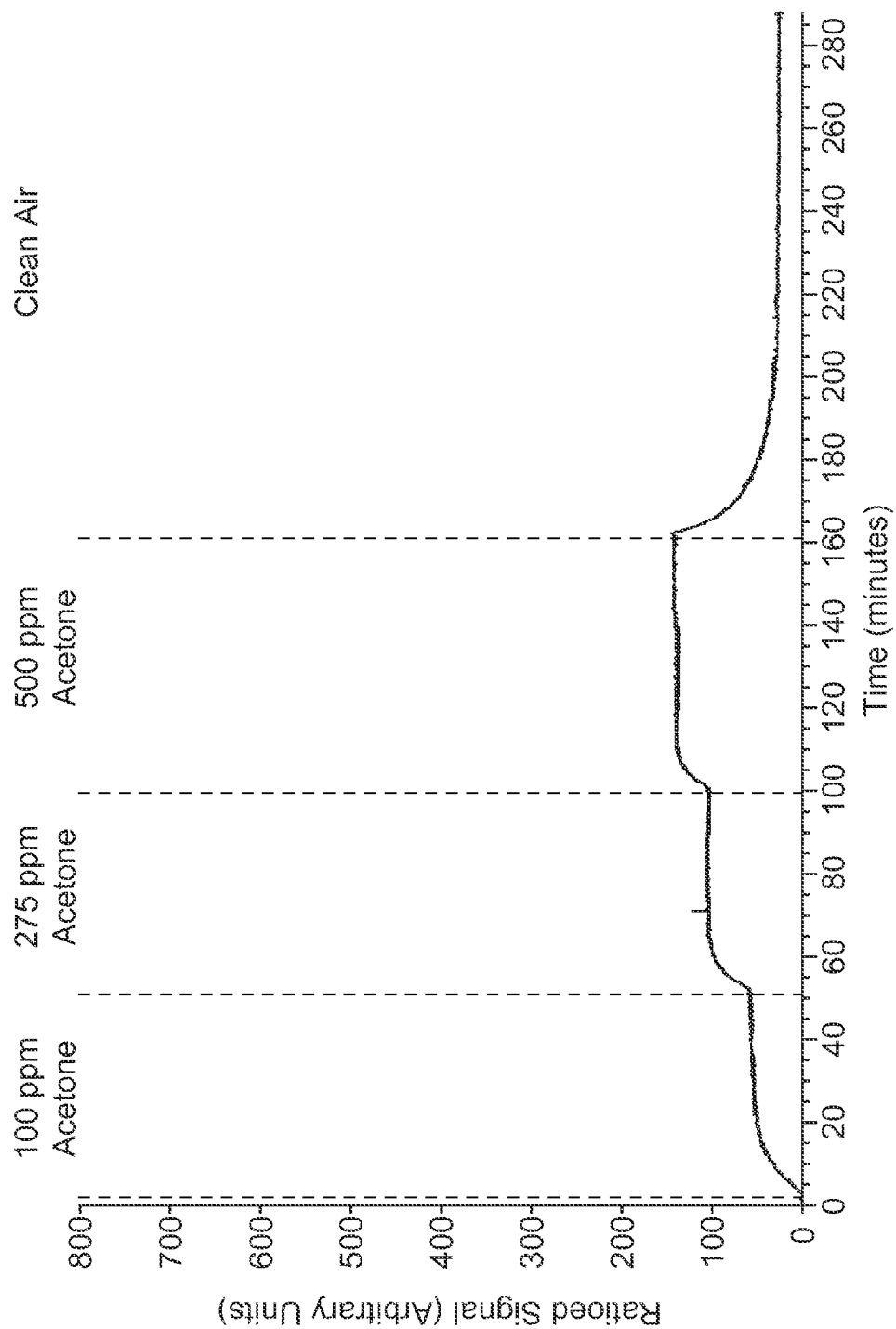
FIG. 13 shows ratioed optical reflectance data from the data of FIG. 12.

Data from these experiments is shown in FIGS. 12 and 13. In FIG. 12, The data labeled Red represents (i.e. as a voltage signal from the photodiode, A/D converted and polled by the microcontroller) light reflected from the sensing element in response to illumination by the red LED. The data labeled Green likewise represents light reflected from the sensing element in response to illumination by the green LED. (The small spikes in FIG. 12 are artifacts resulting from the momentary introduction of stray light into the test chamber). In FIG. 13, the data labeled Ratio is a signal representative of that obtained by ratioing the red signal to the green signal (which operation was performed by the microcontroller).

The tests and test results described above are intended solely to be illustrative, rather than predictive, and variations in the testing procedure can be expected to yield different results. The foregoing detailed description and examples have been given for clarity of understanding only. No unnecessary limitations are to be understood therefrom.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather by the structures described by the language of the claims, and the equivalents of those structures. To the extent that there is a conflict or discrepancy between this specification and the disclosure in any document incorporated by reference herein, this specification will control. This application is a divisional application of U.S. patent application Ser. No. 12/728,883, filed 22 Mar. 2020, and now allowed, which application claimed the benefit of U.S. Provisional Application No. 61/164,496, filed 30 Mar. 2009, both of which are incorporated herein by reference in their entirety.

What is claimed is:

1. An optoelectronic device for monitoring an analyte in an air atmosphere, comprising:
   a housing at least partially defining an interior space and containing at an opening;
   at least one disposable sensing element that is a reflective sensing element that comprises a reflective layer and that is located in the interior space or in the opening of the housing;
   in the interior space, at least one light source arranged to direct light onto the sensing element and at least one light detector arranged to measure an amount of light reflected by the sensing element, wherein the at least one light source and the at least one light detector are arranged in a side by side coplanar configuration on a common printed circuit board contained within the interior space of the device;

and wherein the monitored atmosphere is an air atmosphere and wherein the light directed onto the sensing element and the light reflected therefrom are transmitted through air in the interior space of the device.

2. The device of claim 1 wherein the sensing element comprises a normal axis and wherein the light detector is positioned at the intersection of the normal axis of the sensing element with the printed circuit board; wherein the light source is positioned a distance away from the intersection of the normal axis of the sensing element with the printed circuit board; and wherein the light source is positioned at an angle to the printed circuit board such that light emitted from the light source is directed toward the sensing element.

3. The device of claim 1 wherein the device further comprises at least one optical barrier in between the at least one light source and the at least one light detector that at least partially blocks light from passing directly from the light source to the light detector.

4. The device of claim 3 wherein the optical barrier comprises a holder that assists in holding the light source in position on the printed circuit board.

5. The device of claim 1 wherein the at least one light source and the at least one detector are positioned within 15 mm of each other, measured center to center.

6. The device of claim 1 wherein the device comprises first and second narrowband LED light sources that emit light in nonoverlapping wavelength ranges, and a single broadband light detector.

7. The method of claim 6 wherein the first and second light sources are intermittent sources that flash at separate times with a time delay of at least 1 millisecond therebetween, at a frequency of between approximately 6 per minute and 240 per minute.

8. The device of claim 1 wherein the light that is measured by the light detector is specularly reflected from the sensing element.

9. The device of claim 1 wherein the sensing element is positioned within the interior space of the device and wherein the opening allows analyte to enter the interior space and reach the sensing element.

10. The device of claim 1 wherein the device contains three or more narrowband light sources.

11. An optoelectronic device for monitoring an analyte in an air atmosphere, comprising:

a housing at least partially defining an interior space and containing at an opening;

at least one sensing element that is a reflective sensing element that comprises a reflective layer and that is secured in the opening of the housing;

and, in the interior space, at least one light source arranged to direct light onto the sensing element and at least one light detector arranged to measure an amount of light reflected by the sensing element, wherein when the sensing element is secured in the opening of the housing the opening is occluded such that the interior space of the device comprises a sealed interior space;

and wherein the monitored atmosphere is an air atmosphere and wherein the light directed onto the sensing element and the light reflected therefrom are transmitted through air in the interior space of the device.

12. The device of claim 11 wherein the sensing element is a disposable sensing element that comprises an analyte-responsive layer and further comprises an analyte-permeable, semireflective layer between the analyte-responsive layer and the light detector.

13. The device of claim 12 wherein the sensing element comprises, in order, an analyte-permeable reflective layer, an analyte-responsive layer, a semireflective layer, and an optically clear analyte-impermeable layer, with the optically clear analyte-impermeable layer facing toward the interior space of the device.

14. The device of claim 11 wherein the device comprises an analyte-permeable protective layer positioned adjacent the sensing element on the opposite side of the sensing element from the interior space of the device.

15. The device of claim 11 wherein the sensing element is secured in the opening by mechanical attachment means.

16. The device of claim 11 wherein the device further comprises at least one microcontroller configured to operate the light source and light detector, process signals from the light detector, and notify a user of results obtained from such signal processing.

17. The device of claim 16 wherein the device further comprises, stored in memory, a response curve to which signals processed by the microcontroller are correlatable so as to obtain a concentration value that is representative of the concentration of analyte in the monitored atmosphere.

18. The device of claim 17 further comprising memory storage configured to store any or all of signals from the light detector, processed signals derived therefrom, and concentration values.

19. The device of claim 16 further comprising a transmitter configured to transmit signals to an external receiving station.

* * * * *

UNITED STATES PATENT AND TRADEMARK OFFICE
CERTIFICATE OF CORRECTION

| | | |
|---|---|---|
| PATENT NO. | : 8,817,265 B2 | Page 1 of 1 |
| APPLICATION NO. | : 14/043553 | |
| DATED | : August 26, 2014 | |
| INVENTOR(S) | : John Hulteen | |

It is certified that error appears in the above-identified patent and that said Letters Patent is hereby corrected as shown below:

In the Specification

<u>Column 7</u>
Line 24, Delete "analyte responsive" and insert -- analyte-responsive --, therefor.

<u>Column 13</u>
Line 60, Delete "ore" and insert -- or --, therefor.

<u>Column 18</u>
Line 26, Delete "$\lambda$" and insert -- A --, therefor.

In the Claims

<u>Column 23</u>
Line 33, Claim 7, delete "method" and insert -- device --, therefor.

Signed and Sealed this
Thirtieth Day of December, 2014

Michelle K. Lee
*Deputy Director of the United States Patent and Trademark Office*